United States Patent
Ruppert et al.

(10) Patent No.: US 10,420,712 B2
(45) Date of Patent: *Sep. 24, 2019

(54) MILL BLANKS BASED ON A POLYMERIZED, FRACTURE-TOUGH PROSTHESIS MATERIAL

(71) Applicant: HERAEUS KULZER GMBH, Hanau (DE)

(72) Inventors: Klaus Ruppert, Maintal (DE); Alfred Hohmann, Schmitten (DE); Stephan Dekert, Wehrheim (DE)

(73) Assignee: HERAEUS KULZER GMBH, Hanau (DE)

( * ) Notice: Subject to any disclaimer, the term of this patent is extended or adjusted under 35 U.S.C. 154(b) by 117 days.

This patent is subject to a terminal disclaimer.

(21) Appl. No.: 15/323,129

(22) PCT Filed: Jun. 30, 2015

(86) PCT No.: PCT/EP2015/064875
§ 371 (c)(1),
(2) Date: Dec. 30, 2016

(87) PCT Pub. No.: WO2016/001242
PCT Pub. Date: Jan. 7, 2016

(65) Prior Publication Data
US 2017/0156990 A1 Jun. 8, 2017

(30) Foreign Application Priority Data
Jul. 1, 2014 (DE) .......................... 10 2014 109 233

(51) Int. Cl.
| | | |
|---|---|---|
| *A61C 5/90* | (2017.01) | |
| *A61K 6/083* | (2006.01) | |
| *A61C 13/00* | (2006.01) | |
| *A61K 6/00* | (2006.01) | |
| *A61C 5/77* | (2017.01) | |
| *A61C 1/08* | (2006.01) | |
| *A61C 5/00* | (2017.01) | |
| *A61C 7/02* | (2006.01) | |
| *A61C 7/10* | (2006.01) | |
| *A61C 7/18* | (2006.01) | |
| *A61C 8/00* | (2006.01) | |
| *A61C 13/08* | (2006.01) | |
| *A61D 1/00* | (2006.01) | |
| *A61F 2/30* | (2006.01) | |

(52) U.S. Cl.
CPC .............. *A61K 6/083* (2013.01); *A61C 1/084* (2013.01); *A61C 5/007* (2013.01); *A61C 5/77* (2017.02); *A61C 5/90* (2017.02); *A61C 7/02* (2013.01); *A61C 7/10* (2013.01); *A61C 7/18* (2013.01); *A61C 8/0048* (2013.01); *A61C 13/0004* (2013.01); *A61C 13/0022* (2013.01); *A61C 13/08* (2013.01); *A61C 13/082* (2013.01); *A61D 1/00* (2013.01); *A61F 2/30942* (2013.01); *A61K 6/0005* (2013.01); *A61K 6/0008* (2013.01); *A61F 2002/30952* (2013.01)

(58) Field of Classification Search
CPC . A61C 13/0022; A61C 13/08; A61C 13/0004; A61C 8/0048; A61C 7/18; A61C 7/10; A61C 7/02; A61C 1/084; A61C 5/77; A61C 5/90; A61C 13/082; A61C 5/007; A61K 6/0008; A61K 6/083; A61K 6/0005; A61F 2/30942; A61F 2002/30952; A61D 1/00
See application file for complete search history.

(56) References Cited

U.S. PATENT DOCUMENTS

| | | | |
|---|---|---|---|
| 2006/0217488 A1* | 9/2006 | Renz | ....................... A61K 6/083 525/70 |
| 2009/0192240 A1 | 7/2009 | Benz et al. | |
| 2011/0269894 A1 | 11/2011 | Miyamoto | |
| 2014/0162216 A1 | 6/2014 | Craig et al. | |
| 2015/0305987 A1 | 10/2015 | Pflesser et al. | |
| 2017/0151368 A1* | 6/2017 | Ruppert | .................. A61L 27/16 |

FOREIGN PATENT DOCUMENTS

| | | |
|---|---|---|
| DE | 10 2005 012 825 A1 | 9/2006 |
| DE | 10 2012 013 514 A1 | 5/2014 |
| DE | 10201202269 A1 | 5/2014 |
| EP | 1 702 633 B1 | 1/2013 |

* cited by examiner

*Primary Examiner* — Nathan M Nutter
(74) *Attorney, Agent, or Firm* — Norris McLaughlin, P.A.

(57) ABSTRACT

The subject matter of the invention is a three-dimensional molded body, in particular a milling blank, made of a polymerizable prosthetic material, which is suitable for milling machining by means of CNC and/or CAD/CAM, having a fracture toughness of greater than or equal to 1.9 $Mpa \cdot m^{1/2}$ and a fracture work of greater than or equal to 900 $J/m^2$. The milling blank preferably comprises core-shell particles modified by an elastic phase and is optionally based on a content of urethane (meth)acrylate polymerized into the polymer. Moreover, a subject matter of the invention is the use of the milling blanks for the production of at least parts of dental prosthetic parts, such as a prosthesis, artificial teeth, bridges, or of orthodontic appliances and instruments in medical field.

8 Claims, 1 Drawing Sheet

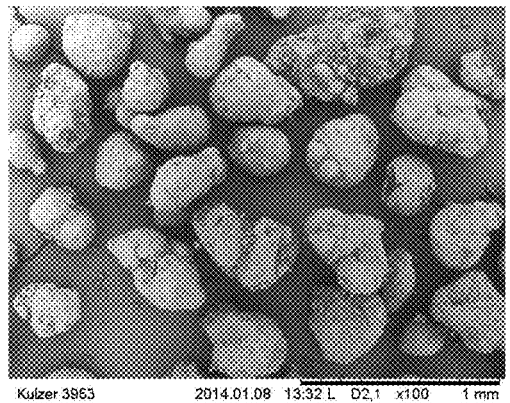
FIG.: 1a
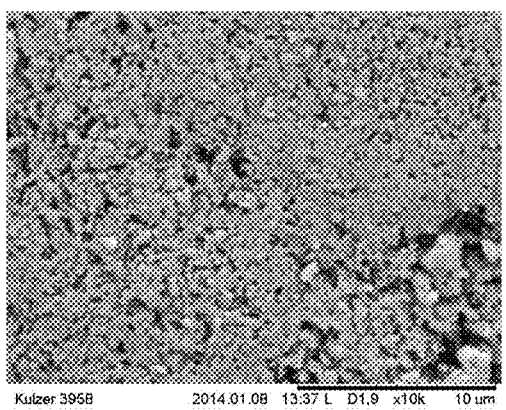
FIG.: 1b
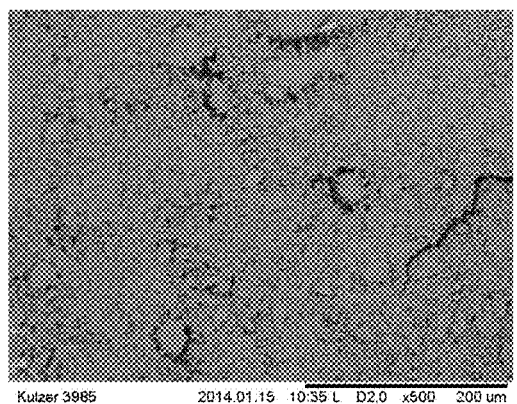
FIG.: 1c
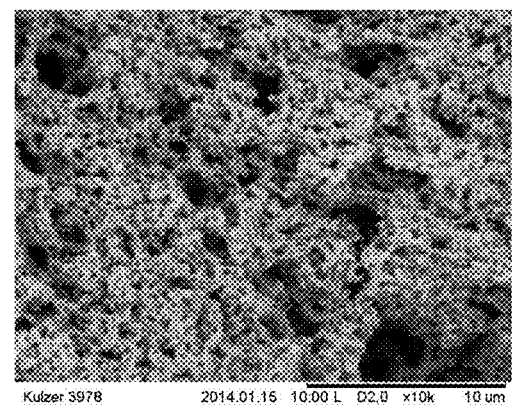
FIG. 1d
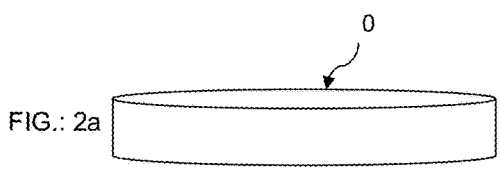
FIG.: 2a
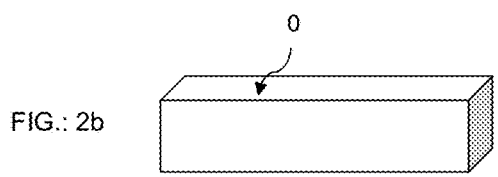
FIG.: 2b

MILL BLANKS BASED ON A POLYMERIZED, FRACTURE-TOUGH PROSTHESIS MATERIAL

This application is a 371 of PCT/EP2015/064875, filed Jun. 30, 2015, which claims foreign priority benefit under 35 U.S.C. § 119 of German Patent Application No. 10 2014 109 233.3, filed Jul. 1, 2014, the disclosures of which are incorporated herein by reference.

Subject matter of the invention is a three-dimensional moulded body, in particular a milling blank, made of a polymerisable prosthetic material, which is suitable for ablative machining by means of CNC and/or CAD/CAM, having a fracture toughness of greater than or equal to 1.9 MPa·m$^{1/2}$ and a total fracture work of greater than or equal to 900 J/m$^2$. The milling blank preferably comprises core-shell particles modified by an elastic phase and is optionally based on a content of urethane (meth)acrylate polymerised into the polymer. Moreover, a subject matter of the invention is the use of the milling blank for the production of at least parts of dental prosthetic parts, such as a prosthesis, occlusal splints, surgical guides, artificial teeth, crowns, bridges, or of orthodontic appliances and instruments in medical field. Particularly preferably, the milling blank is suitable for machining by means of milling.

Due to the limited motor skills of prosthesis wearers, who are usually more advanced in age, protheses occasionally are dropped onto a hard surface (tiles, washbasin), which may cause them to chip, or to break. Said chipping is associated with additional work and additional costs for the dental laboratory and is therefore undesirable. Moreover, in particular in the event of implant-supported dental prostheses, appreciably higher chewing forces may cause the prosthesis getting damaged.

For these reasons, there is a need to have a prosthesis material that tolerates short-term loads, such as the aforementioned, short-term high mechanical loads, without the material getting damaged. These prosthesis materials are referred to as so-called high-impact materials. Requirements for said materials are described in DIN ISO 20795-1. Products meeting these requirements have been on the market for some time, but are all members of the group of hot-curing prosthesis materials. Moreover, there is a need for milling blocks for machining by means of CAD/CAM. Thus, for certain prosthetic applications, such as implant-supported prostheses, occlusal splints, or orthodontic appliances, there is a need for materials that also cope with brief high mechanical loads without the material getting damaged. However, up to now, only PMMA-milling blocks are known for CAD/CAM-machining. But these materials are not always able to cope with chewing loads of the aforementioned prosthetic parts or orthodontic appliances.

It was an object of the invention to provide a millable material, preferably in the form of a milling blank, such as a material being suitable in the medical field, which exceeds the requirements concerning fracture toughness of norm DIN ISO 20795-1. Furthermore, it was an object for the millable material to be present in the form of a milling blank. Moreover, it was an object for the milling blank to meet the aesthetic requirements for the transparency of prosthetic materials and to contain no or only a very small number of bubbles. It was another object to provide a highly fracture-tough material in the form of a milling blank, in particular a milling blank made of a prosthetic material, whose transparency is not affected compared with the basis material. It was another object to provide the milling blank, possibly also, multi-coloured, i.e. flesh-coloured and tooth-coloured.

It has surprisingly been found, that a milling blank made of a material, in particular a prosthetic material, having the required properties concerning fracture toughness and, preferably, concerning the requirements for transparency, can be provided. Preferably, the milling blank is based on a polymerised prosthetic material comprising core-shell particles and, optionally, urethane (meth)acrylate polymerised into the polymer.

Moreover, increased requirements are made on millable materials concerning the properties of the surface and the surfaces received after the milling process. Thus, no microcracks shall occur through the machining.

Liquid additives being potentially suitable for increasing of the fracture toughness, such as, for example, acrylonitrile-butadiene copolymer, tended to show yellowing of the prosthetic material. This is typically done in the presence of oxidizing substances, such as, for example, peroxides or atmospheric oxygen. Moreover, the liquid additives, such as, for example, silicone acrylates, have a refractive index being markedly different from PMMA and thus typically result in forming an opaque material. The urethane acrylate-based liquid additives, such as, for example, urethane acrylate, often lead to an improvement of the fracture toughness of materials, but do not meet the minimum requirements concerning fracture toughness of ISO 20795-1. Another disadvantage of some additives results in water absorption during the polymerisation process resulting in an undesired whitening of the prosthesis material while worn.

The object of the invention was met by a milling blank according to claim 1, as well as, by a method for the production of the milling blank according to claim 13, whereby specific embodiments are described in detail in the sub-claims and in the specifications.

Hence, subject matter of the invention is a milling blank made of polymeric prosthetic material, preferably consisting of polymeric prosthetic material, in particular an polymerised prosthetic material, in the form of a three-dimensional moulded body, in particular a CAD/CAM-milling blank, having a fracture toughness of greater than or equal to 1.9 MPa·m$^{1/2}$ a total fracture work of greater than or equal to 900 J/m$^2$, in particular, the milling blank has a fracture toughness of greater than or equal to 2.3 MPa·m$^{1/2}$ and, optionally, a total fracture work of greater than or equal to 1000 J/m$^2$.

BRIEF DESCRIPTION OF THE DRAWINGS

The invention will now be described in greater detail with reference to the drawings, wherein:

FIG. 1a is a Scanning Electron Microscope (SEM) image at 100× magnification of core-shell particles.

FIG. 1b is a SEM image at 10,000× magnification of core-shell particles.

FIG. 1c is a SEM image at 100× magnification of an additive being suspended in methyl methacrylate (MMA).

FIG. 1d is a SEM image at 10,000× magnification of an additive being suspended in MMA.

FIG. 2a is an example of a milling blank (0).

FIG. 2b is an example of another milling blank (0).

The milling blank according to the invention can preferably be designed multi-coloured, in particular defined areas are designed in tooth colours and/or defined areas are designed colour-adjusted to the gingiva, in particular, said areas are in flesh colours. According to a further alternative, the milling blank can be purely designed in tooth colours or purely colour-adjusted to the gingiva. In this context, both the tooth colour and the flesh colour can be adjusted to natural colour gradients. Furthermore, the milling blanks according to the invention preferably comprises (i) core-shell particles modified by an elastic phase and/or (ii) at least one polymer comprising at least one urethane (meth)acrylate polymerised into the polymer.

The core-shell particles preferably comprise primary particles having an average particle size of less than or equal to $d_{50} \leq 500$ nm to 10 nm, preferably from 100 to 450 nm, particularly preferably from 200 to 400 nm. The primary particles of the core-shell particles can be present as aggregates of primary particles. Said aggregates preferably have an average particle size of less than or equal to $d_{50} \leq 400$ μm (micrometer).

For setting the properties of the milling blank, it can also be preferred for the milling blank to comprise (i) 0.001 to 20% by weight of core-shell particles modified by at least one elastic phase, based on the total composition, preferably it comprises up to 10% by weight of core-shell particles, particularly preferably up to 5% by weight.

It is further preferred for the milling blank to have up to (ii) 0.001 to 20% by weight of at least one urethane (meth)acrylate polymerised into the polymer, in particular one urethane dimethacrylate, based on the total composition, preferably up to 10% by weight, particularly preferably up to 5% by weight. Preferably, the urethane methacrylate is polymerised into the prosthetic material.

According to the invention, the object is met by synergistical use of core-shell particles and at least one urethane methacrylate in the prosthetic base material. Combining core-shell particles in the liquid monomer component in conjunction with at least one urethane acrylate or one urethane methacrylate in the liquid can achieve particularly good results in the polymerised prosthesis material. The selection of specific core-shell particles having a refractive index similar to that of the polymerised prosthetic material ensured high transparency of the prosthesis material. The core-shell particles therefore preferably have a refractive index of about 1.49 (R.I. ~1.4900).

Particularly preferred core-shell particles according to the invention are present in aggregated form. The objects can be met by use of aggregated core-shell particles (irregularly shaped aggregates, $d_{50}$~50-400 μm, in particular 50-300 μm), the primary particle size is approximately 200-400 nm. Probably, the core-shell particles are present in aggregated form due to surface interaction in the solid. The additive is mixed with the liquid and forms a stable suspension that just weakly sediments within a few weeks. As a result of suspending in MMA, the aggregates relatively quickly degrade into the primary particles, which are then homogenously distributable and, preferably, are present in the milling blanks in homogenously distributed manner.

By inventive use of the core-shell particles as a high-impact additive in conjunction with at least one urethane acrylate, preferably one urethane methacrylate, it is possible to produce prosthesis materials meeting the requirements concerning high-impact properties of ISO 20795-1. Moreover, a prosthesis material having its flexural strength and E-modulus in the same order as non-high-impact materials and, at the same time, being highly transparent and colour-stable can be provided. The prostheses according to the invention do not show any whitening by contact with water-containing materials, such as, for example, duplicating gels or plasters, during and after polymerisation process.

In order to distinguish prosthetic materials, as used as a material of the milling blank, from usual dental materials, it is emphasized that prosthetic materials comprise substantial amounts of polymeric powdered components, such as PMMA (Poly(meth)methylacrylate) and/or (Poly(ethyl) methacrylate), in particular of greater than or equal to 50% by weight in the total composition. Dental materials for the production of fillings are largely based on polymerisable monomers preferably being present in an amount of less than 35% by weight in the polymerisable composition.

Usual prosthetic materials are usually provided in a kit having a powdered component and a liquid component. According to the invention, a milling blank is provided in the form of a polymerised prosthetic material, optionally being colour-adapted to dental situation and/or gingiva.

According to the invention, core-shell particles, possibly being present as aggregates, whereby, however, said aggregates can be separated into single particles during the short swelling time, in particular degrade into single particles after adding the liquid monomer component, are particularly well-suited for use.

According to a further embodiment, the milling blanks according to the invention can additionally comprise one or more substance(s) from the group consisting of filler, pigments, stabilizers, regulators, antimicrobial additives, UV-absorbing agents, thixotroping agents, catalysts and cross-linkers.

Milling blanks according to the invention preferably comprises greater than or equal to 55% by weight of PMMA, based on the total composition, in particular greater than 60, 70, 75, 80, 85, 90, 95, 97% by weight PMMA, based on the total composition, and, optionally, 0.001 to 5% by weight core shell particles, preferably 0.5 to 2% by weight, particularly preferably 0.5 to 1.5% by weight. Furthermore, it can be preferred for the milling blank to comprise, in addition, 0.001 to 10% by weight urethane (meth)acrylate, preferably 0.5 to 5% by weight, particularly preferred 0.5 to 2% by weight.

According to a further particularly preferred embodiment, the milling blanks are based on a polymerised, fracture-tough prosthetic material preferably being obtainable by a method according to the invention. According to an alternative, a subject matter of the invention is a method for the production of a polymerised prosthetic material, as well as a prosthetic material, in particular a prosthetic material in the form of a milling blank, in which the components A) at least one liquid monomer component, and B) at least one powdered component, of the prosthetic material, are being mixed and subsequently polymerised.

The invention also relates to a method for the production of a polymerisable prosthetic material in the form of a three-dimensional moulded body, preferably in the form of a milling blank, in which a polymerisable prosthetic material comprising components (A) and/or (B), whereby component A) is at least one liquid monomer component, and B) is at least one powdered component, and the polymerisable prosthetic material comprises in component (A) and/or (B) (i) core-shell particles modified by an elastic phase, and (ii) at least one urethane (meth)acrylate, the components (A) and/or (B) (a) are being mixed, (b) are being transferred into a three-dimensional mould, in particular into the mould of a half-finished product mould of milling blanks or in the mould of milling blanks, (c) and, subsequently, the polymerisable prosthetic material is being polymerised.

Preferably, the method is proceeded such that the mixture comprising the A) monomer component and B) powdered component, in particular as being a polymerisable prosthetic material, is being introduced into a negative mould, such as a casting mould, in particular a half-finished product mould of milling blanks, or a negative form of a milling blank, or at least one dental prosthetic moulded body, and being polymerised, in particular at elevated pressure, in particular greater than 2 bar, such as 2, 5 to 10 bar, preferably 2 to 4 bar.

A three-dimensional mould according to the invention shall be understood to preferably mean half-finished product moulds of milling blanks, such as bar-shaped, disc-shaped, cylinder-shaped, or further half-finished product moulds and finished product moulds of milling blanks known to the person skilled in the art, particularly preferred are disc-shaped, preferably cylinder-shaped milling blanks. Cylinder-shaped shall be understood to mean mathematical or even circular cylindrical shapes, such as circular discs. The milling blanks can also be cuboid-shaped or have another polyhedral shape and/or any suitable three-dimensional shape.

In this context, according to the invention, it is preferred for the A) monomer component and the B) powdered component to be mixed in the method at a weight ratio of 1:50 to 50:1, in particular at a weight ratio of 8 to 11 powdered component to 5 to 8 monomer component.

Component A), the liquid monomer component, preferably include at least one monomer or a mixture of monomers from a) methylmethacrylate, ethylmethacrylate, propylmethacrylate, butylmethacrylate, n-hexylmethacrylate, 2-phenoxyethyl methacrylate, isobornylmethacrylate, isodecylmethacrylate, polypropylene glycol monomethacrylate, tetrahydrofurylmethacrylate, methylacrylate, ethylacrylate, propylacrylate, butylacrylate, n-hexylacrylate, 2-phenoxyethylacrylate, isobornylacrylate, isodecylacrylate, polypropylene glycol monoacrylate, tetrahydrofurylacrylate, hydroxyethylacrylate, hydroxypropylacrylate, hydroxyethyl methacrylate, hydroxypropylmethacrylate, benzyl-, furfuryl- or phenyl(meth)acrylate, a mixture comprising at least one of said (meth)acrylates and/or copolymers comprising one or at least two of the afore-mentioned monomers, and/or b) two- and/or multi-crosslinkers comprising 1,4-butandiol dimethacrylate (1,4-BDMA) or pentaerythritol tetraacrylate, bis-GMA monomer (bisphenol-A-glycidylmethacrylate), triethylene glycol dimethacrylate (TEGDMA) and diethylene glycol dimethacrylate (DEGMA), tetraethylene glycol di(meth)acrylate, decanediol di(meth)acrylate, dodecandiol di(meth)acrylate, hexyldexandiol di(meth)acrylate, trimethylolpropane tri(meth)acrylate, pentaerythritol tetra (meth)acrylate, as well as butanediol di(meth)acrylate, ethylene glycol di(meth)acrylate, polyethylene glycol di(meth) acrylate, ethoxylated/propoxylated bisphenol-A-di(meth) acrylate, a mixture comprising at least one of said (meth) acrylates and/or copolymers comprising one or at least two of the afore-mentioned monomers.

Component B), the powdered component, preferably include polymeric particles, comprising polymers in the form of polymer powder comprising polyalkyl(meth)acrylates, optionally being crosslinked and being present as homopolymer or copolymer, whereby the polymers are based on at least one monomer comprising a (meth)acrylat group, selected from methylmethacrylate, ethylmethacrylate, propyl methacrylate, butyl methacrylate, n-hexyl methacrylate, 2-phenoxyethylmethacrylate, isobornylmethacrylate, isodecylmethacrylate, polypropylene glycol mono methacrylate, tetrahydrofurylmethacrylate, methylacrylate, ethylacrylate, propylacrylate, butylacrylate, n-hexylacrylate, 2-phenoxyethylacrylate, isobornylacrylate, isodecylacrylate, polypropylene glycol monoacrylate, tetrahydrofurylacrylate, hydroxyethylacrylate, hydroxypropylacrylate, hydroxyethylmethacrylate, hydroxypropylmethacrylate, a mixture comprising at least one of said (meth)acrylates and/or copolymers comprising one or at least two of the afore-mentioned monomers, polyamide particles, polyamide fibers, particularly preferred is polymethylmethacrylate (PMMA). Moreover, the polymeric particles can also comprise mixtures of dental monomers, such as, for example, MMA, and, additionally, at least one crosslinker.

Powdered components B) comprising polymethylmethacrylate (PMMA) beads as polymeric particles and/or splitter polymers, as well as copolymers comprising as comonomers, being polymerised into the copolymer, styrene, alpha-methylstyrene, vinyltoluene, substituted vinyltoluene, such as vinylbenzylchloride, vinylhalogenide, such as vinylchloride, vinylester, such as vinylacetate, heterocyclic vinyl compounds, such as 2-vinylpyridine, vinylpropionate, butadiene, isobutylene, 2-chlorobutadiene, 2-methylbutadiene, vinylpyridine, cyclopentene, (meth)acrylic acid ester, such as methylmethacrylate, ethylmethacrylate, butylmethacrylate, butylacrylate and hydroxyethylmethycrylate, moreover acrylonitrile, maleic acid and maleic acid derivatives, such as, for example, maleic acid anhydride, fumaric acid and fumaric acid derivatives, such as fumaric acid esters, acrylic acid, methacrylic acid, acryl(meth)acrylates, such as benzylmethacrylate or phenylmethacrylate, as well as, optionally, mixtures of said comonomers.

Furthermore, the prosthetic material comprises in components—(A) and/or (B) (iii) at least one initiator or one initiator system for autopolymerisation, radiation curing, in particular UV-curing, hot-polymerisation or dual-curing.

According to a particularly preferred alternative, a subject matter of the invention is a polymerised prosthetic material, obtainable by a method according to a method according to the invention, that is present in the form of a three-dimensional moulded body, in particular in the form of a milling blank or of a half-finished product mould.

In this context, it is more preferred for the polymerised prosthetic material to have a fracture toughness $\geq 1.9$ MPa·m$^{1/2}$ of and a total fracture work of $\geq 900$ J/m$^2$.

The milling blank according to the invention made of the prosthetic material, as being polymerised prosthetic material, preferably has a fracture toughness ($k_{max}$; maxi-mum stress intensity factor) of greater than or equal to 1.9 MPa·m$^{1/2}$, in particular of greater than or equal to 2 MPa·m$^{1/2}$, and, preferably at the same time, a total fracture work ($W_f$) of greater than or equal to 900 J/m$^2$. Particularly preferably, the fracture toughness is greater than or equal to ($\geq$) 2.1 MPA·m$^{1/2}$, preferably $\geq 2.3$ MPA·m$^{1/2}$, $\geq 2.4$ MPa·m$^{1/2}$. Furthermore, it is preferred for the fracture work to be, at the same time, greater than $\geq 900$ J/m$^2$, in particular greater than $\geq 950$ J/m$^2$, $\geq 1000$ J/m$^2$, particularly preferably greater than or equal to 1030 J/m$^2$. Particularly preferably, the flexural strength is, in addition, greater than 65 MPa, particularly preferably greater than 70 MPa, more preferably greater than 75 Mpa. A particularly preferred prosthetic material has a fracture toughness of >2.3 MPa·m$^{1/2}$ and a total fracture work of >1000 J/m$^2$.

Furthermore, it is preferred that the transparency of the unpigmented, polymerised milling blanks, and the prosthetic parts or orthodontic appliances made thereof, is in the range of greater than or equal to 85%, in particular of greater than or equal to 90%. (measured against plates having a thickness of 3 mm)

According to an embodiment, a subject matter of the invention is an autopolymerisable and/or cold-polymerisable, or hot-polymerisable two-component prosthetic base material, in particular a polymerisable prosthetic material, comprising A) at least one liquid monomer component, B) at least one powdered component, in particular for use in the production of milling blanks, whereby the prosthetic material comprises in components (A) and/or (B)

(i) at least one initiator or initiator system for autopolymerisation and/or cold-polymerisation or hot-polymerisation, (ii) core-shell particles modified by an elastic phase, and (iii) at least one urethane (meth)acrylate, in particular one urethane dimethacrylate, preferably one bis(methacryloxy-2-ethoxycarbonylamino)alkylene, Diurethane acrylate oligomer, alkyl-functional urethane dimethacrylate oligomers, aromatically functionalised urethane dimethacrylate oligomers, aliphatic unsaturated urethane acrylates, bis(methacryloxy-2-ethoxycarbonylamino)-substituted polyether, aromatic urethane diacrylate oligomers, aliphatic urethane diacrylate oligomers, mono-functional urethane acrylates, aliphatic urethane diacrylates, hexa-functional aliphatic urethane resins, aliphatic urethane triacrylates, UDMA, aliphatic urethane acrylate oligomers, unsaturated aliphatic urethane acrylate.

As explained below, the components of the initiator system may be divided between components A) and B). Another subject matter of the invention is a method for the production of the milling blank from the afore-mentioned polymerisable prosthetic material, as well as a three-dimensional blank obtainable by mixing, forming and polymerising the polymerisable prosthetic material.

Particularly preferably, component (A) comprises at least one liquid monomer component, (i) at least one initiator or one initiator system for autopolymerisation or hot-polymerisation, or one part of the components of the initiator system, (ii) core-shell particles modified by at least one elastic phase, and (iii) at least one urethane (meth)acrylate, in particular urethane dimethacrylate.

In this context, it is particularly preferred for component (ii) core-shell particles modified by at least one elastic phase to be present at 0.001 to 20% by weight, in particular up to 10% by weight, preferably up to 5% by weight, based on the total composition of component (A), and for (iii) at least one urethane (meth)acrylate, in particular one urethane dimethacrylate, to be present at 0.001 to 20% by weight, in particular up to 10% by weight, more preferably up to 5% by weight, based on the total composition of component (A) (i.e. on 100% by weight of component (A)).

Despite the added high-impact modifier (core-shell particles and urethane (meth)acrylate) the milling blank according to the invention made of prosthetic material, in particular made of polymerised prosthetic material, does not show negative influence on Suntest according to ISO 20795-1. The core-shell particles are also referred to as high-impact modifier.

Particularly preferred milling blanks made of prosthetic materials preferably have core-shell particles, in which the distribution of the elastic phase of the modified core-shell particles is selected from possibilities a to d: a) elastic phase as core (e.g. made of butylacrylate) in solid outer shell (e.g. made of PMMA) (core-shell particles; b) multiple elastic phases as cores in a solid matrix; c) core-shell particles from a), distributed in solid matrix, and d) solid core with elastic phase as outer shell.

Core-shell particles according to the invention can also have the following multi-layer structure, e) an inlying core with multiple layers as shells and one outer shell, whereby, in particular, (i) at least one of the shells, in particular the outer shell, is solid and the remaining shells and the core, each independently, consists of elastic phases. In alternatives, the elastic phases and the solid phases may be otherwise divided between the shells and the core.

Furthermore, preferred core-shell particles have a refractive index similar to that of the polymerised prosthesis material. Preferably, the refractive index of the core-shell particles is about 1.4900 having a total variability of the present value of plus/minus 0.02, in particular +/−0.01. According to the invention, particularly preferred core-shell particles are present in aggregated form. In this context, the aggregates of the core-shell particles, which can be randomly shaped, as being an irregularly shaped aggregate, have an average diameter of $d_{50}$~50-300 μm. The preferred size of the primary particle size is less than 500 nm, in particular up to 100 nm, preferably from 200-400 nm. Core-shell particles having a primary particle size of less than or equal to 200 nm to 2 nm, such as between 150 to 10 nm, can also be used as core-shell particles.

Preferably the core-shell particles have a refractive index of 1.48 to 1.60, in particular of 1.49 to 1.55. Particularly preferably, the refractive index of the core-shell particles is in the range of the refractive index of PMMA, PEMA, preferably the refractive index is therefore about 1.48 to 1.50.

Core-shell particles whose density is 0.9 to 1.5 g/ml, in particular 0.95 to 1.4 g/ml are also preferred. Preferably, the bulk density is, at the same time, 0.1 to 0.6 g/ml.

A solid outer shell, solid matrix and/or solid core shall be understood to mean a material, which preferably has a lower elasticity than the material of the elastic phase. Preferably, the elasticity of the solid materials is at least 40% less than that of the elastic phase. Preferred inorganic solid cores show substantially no deformation under the influence of a force, while the organic solid materials undergo an appreciably lower deformation under the influence of a force than the elastic phase. The solid materials as being a solid outer shell, solid matrix and/or solid core stabilize the elastic phase in its shape. An elastic phase is formed by at least one elastic material, which undergoes a reversible deformation under the influence of a force. The deformation of the elastic phase advantageously is fully reversible without force effect.

Particularly preferably, the powdered component comprises polymethylmethacrylate (PMMA) beads as polymeric particles and/or splitter polymers, in particular having particle sizes of 10-100 μm, and/or is based on copolymers comprising as comonomers, being polymerised into the copolymer, styrene, alpha-methylstyrene, vinyltoluene, substituted vinyltoluene, such as vinylbenzylchloride, vinylhalogenide, such as vinylchloride, vinylester, such as vinylacetate, heterocyclic vinyl compounds, such as 2-vinylpyridine, vinylpropionate, butadiene, isobutylene, 2-chlorobutadiene, 2-methylbutadiene, vinylpyridine, cyclopentene, (meth)acrylic acid ester, such as methylmethacrylate, ethylmethacrylate, butylmethacrylate, butylacrylate and hydroxyethylmethycrylate, moreover acrylonitrile, maleic acid and maleic acid derivatives, such as, for example, maleic acid anhydride, fumaric acid and fumaric acid derivatives, such as fumaric acid esters, acrylic acid, methacrylic acid, as well as acryl(meth)acrylates, such as benzylmethacrylate or phenylmethacrylate, as well as, optionally, mixtures of said comonomers.

Optionally, the powdered component can additionally comprise: b) inorganic fillers comprising pyrogenic or precipitated silicas, dental glasses, such as aluminosilicate glasses or fluoroaluminosilicate glasses, bariumaluminium silicate, strontium silicate, strontium borosilicate, lithium silicate, lithiumaluminium silicate, phyllosilicates, zeolites, amorphous spherical fillers based on oxide or mixed oxide, in particular mixed oxides of $SiO_2$ and $ZrO_2$, glass fibres and/or carbon fibers, as well as mixtures comprising said powdered components a) and b).

The b) inorganic fillers are usually used in amounts of 0 to 10% by weight, preferably of 0.0001 to 3% by weight, based on the total prosthetic plastic composition and/or the sum of components (A) and (B). In component (B) they are usually present in the range of 0 to 20% by weight, preferably of 0.001 to 10% by weight, based on the total composition of component (B) of 100% by weight.

Polymeric particles, which are based on at least one (meth)acrylate monomer having just one (meth)acrylate group or which are based on a mixture of at least two of said (meth)acrylate monomers are also in the scope of the invention.

Core-shell particles according to the invention preferably comprise as elastic phase at least one poly-(n-butyl acrylate) PBA, butadiene-styrene copolymer, nitrile-butadiene copolymer, silicon rubber-(graft copolymers), polyurethane polymer, polyolefin-based polyurethane (polybutadiene-based polyurethane), which can preferably be present in MMA. The particle size of the core-shell particles can be less than or equal to 500 nm, such as between 50 nm to 500 nm, in particular less than or equal to 400 nm to 100 nm, or, alternatively, less than 100 nm to 2 nm, the elastic phase can also be based on polydimethylsiloxane-modified polyurethanes and/or epoxy-functionalised elastic phases.

Core-shell particles according to the invention comprise as solid shell, solid core and/or solid matrix at least one (meth)acrylate polymer, preferably one alkyl(meth)acrylate polymer, such as PMMA, polystyrene, an epoxy-functionalised core, as well as homo- or co-condensates of the afore-mentioned polymers.

Particularly preferred core-shell particles, in conjunction with urethane (meth)acrylate, provide the polymerised prosthetic material with high impact properties, with a fracture toughness of $\geq 1.9$ MPa·m$^{1/2}$, preferably $\geq 2$ MPa·m$^{1/2}$, and a fracture work of $\geq 900$ J/m$^2$. Preferred core-shell particles comprise aggregates having $d_{50} < 400$ µm and primary particle sizes of $d_{50}$ less than 500 nm. More preferably, the primary particles of the core-shell particles can be greater than or equal to 100 nm, in particular as a $d_{50}$-value.

Core-shell particles comprising an elastic core comprising acrylate polymers with solid outer shell, in particular having a particle size of less than 1 micrometer, are also suitable. More preferably, the core-shell particles have groups being reactive against polymerisable monomers, preferably, the outer shell is functionalised by (meth)acrylate groups. Alternative core-shell particles comprise as solid core a silicon dioxide and an elastic shell comprising at least one nitrile-butadiene copolymer. Further core-shell particles may be present in a monomer liquid.

According to the invention, di-functional and multi-functional urethane (meth)acrylates, such as, in particular, urethane di(meth)acrylate, are preferably suitable as urethane (meth)acrylate, particularly preferably, the at least one (iii) urethane dimethacrylate (UDMA) is selected from linear alkyl- or branched alkyl-functionalised urethane dimethacrylates, urethane dimethacrylate-functionalised polyethers, in particular bis(methacryloxy-2-ethoxycarbonylamino) alkylene, bis(methacryloxy-2-ethoxycarbonylamino)-substituted polyether, preferably 1,6-bis(methacxryloxy-2-ethyxycarbonylamino)-2,4,4-trimethylhexane. Suitable urethane (meth)acrylates are available under the following brand names: Ebecryl 230 (aliphatic urethane diacrylate), Actilane 9290, Craynor 9200 (Diurethane acrylate oligomer), Ebecryl 210 (aromatic urethane diacrylate oligomers), Ebecryl 270 (aliphatic urethane diacrylate oligomers), Actilane 165, Actilane 250, Genomer 1122 (monofunctional urethane acrylate), Photomer 6210 (cas no. 52404-33-8, aliphatic urethane diacrylate), Photomer 6623 (hexa-functional aliphatic urethane resin), Photomer 6891 (aliphatic urethane triacrylate), UDMA, Roskydal LS 2258 (aliphatic urethane acrylate oligomer), Roskydal XP 2513 (unsaturated aliphatic urethane acrylate).

Furthermore, a subject matter of the invention is a milling blank comprising prosthetic material being based on reaction of at least one (A) liquid monomer component and one (B) powdered component, whereby the (A) liquid monomer component comprises at least one monomer, in particular a mixture of monomers from a) methylmethacrylate, ethylmethacrylate, propylmethacrylate, butylmethacrylate, n-hexylmethacrylate, 2-phenoxyethyl methacrylate, isobornylmethacrylate, isodecylmethacrylate, polypropylene glycol monomethacrylate, tetrahydrofurylmethacrylate, methylacrylate, ethylacrylate, propylacrylate, butylacrylate, n-hexylacrylate, 2-phenoxyethylacrylate, isobornylacrylate, isodecylacrylate, polypropylene glycol monoacrylate, tetrahydrofurylacrylate, hydroxyethylacrylate, hydroxypropylacrylate, hydroxyethyl methacrylate, hydroxypropylmethacrylate, benzyl-, furfuryl- or phenyl(meth)acrylate, a mixture comprising at least one of said (meth)acrylates and/or copolymers comprising one or at least two of the afore-mentioned monomers, and/or b) two- and/or multi-crosslinkers (>2) comprising 1,4-butandiol dimethacrylate (1,4-BDMA) or pentaerythritol tetraacrylate, bis-GMA monomer (bisphenol-A-glycidylmethacrylate), triethylene glycol dimethacrylate (TEGDMA) and diethylene glycol dimethacrylate (DE-GMA), tetraethylene glycol di(meth)acrylate, decanediol di(meth)acrylate, dodecandiol di(meth)acrylate, hexyldexandiol di(meth)acrylate, trimethylolpropane tri(meth)acrylate, pentaerythritol tetra(meth)acrylate, as well as butanediol di(meth)acrylate, ethylene glycol di(meth)acrylate, polyethylene glycol di(meth)acrylate, ethoxylated/propoxylated bisphenol-A-di(meth)acrylate, a mixture comprising at least one of said (meth)acrylates and/or copolymers comprising one or at least two of the afore-mentioned monomers.

Suitable alkylmethacrylates for liquid component (A) are methyl-, ethyl-, n-propyl-, i-propyl-, n-butyl-, t-butyl-, i-butyl-, benzyl- and furfurylmethacrylate or mixtures thereof. Of these, methylmethacrylate is particularly preferred.

Preferably, the (A) liquid monomer component comprises a.1) >85% by weight of at least one mono-functional (meth)acrylate-functional monomer component, in particular 85 to 90% by weight, a.2) 0-15% by weight of at least one difunctional di(meth)acrylate-functional monomer component, in particular 0.01 to 15% by weight, 1 to 10% by weight, and a.3) 0-10% by weight of at least one (meth)acrylate-functional tri-functional (meth)acrylate or one multi-functional (meth)acrylate, in particular 0.01 to 10% by weight, preferably 1.0 to 8% by weight, b) 0-5% by weight of stabilizers and activators, initiators, in particular 0.01 to 5% by weight, preferably 0.1 to 3% by weight, c) from 0.001 to 20% by weight urethane (meth)acrylate, in particular 0.01 to 10% by weight, preferably from 0.5 to 5% by weight, particularly preferably from 0.01 to 3% by weight, d) from 0.001 to 20% by weight core-shell particles, in particular 0.001 to 10% by weight, preferably 1 to 10% by weight, particularly preferably 0.001 to 5% by weight, preferably between 0.5 to 5% by weight, whereby the total composition of liquid monomer component A) totals 100% by weight. The total composition of all components of the powdered component (B) totals 100% by weight, as well. The core-shell particles are usually suspended in the monomers.

According to the invention, the total composition of the powdered component (B) is composed as follows:

b.1) from 100% by weight of polymeric particles and, optionally, inorganic fillers or a mixture thereof, the content can preferably be composed as follows: from 100 to 80% by weight polymeric particles, such as PMMA, PEMA, from 0 to 20% by weight inorganic fillers, such as dental glasses, metal oxide basis or mixed oxide basis ($SiO_2$, $ZrO_2$ and/or $TiO_2$), in particular 0.01 to 10% by weight, b.2) 0-5% by weight of at least a part of an initiator system, in particular 0.01 to 4% by weight, and b.3) 0-5% by weight of pigments, excipients, stabilizers, or mixtures comprising at least one of the afore-mentioned components, in particular 0.01 to 4% by weight, the afore-mentioned total composition of the powdered component totals 100% by weight.

Preferably, powdered polymeric components, such as PMMA, of different particle sizes can possibly be used, as homo- and/or copolymers: a) homopolymer bead 1 ($d_{50}$~40-50 μm) and b) bead 2 ($d_{50}$~55-70 μm), and, optionally, copolymer c) bead 3 ($d_{50}$~40-50 μm).

The total composition (A) with 100% by weight and the total composition (B) with 100% by weight are being mixed at a weight ration of (A) to (B) of 1 to 20 to 20 to 1, preferably at a weight ratio of (A) to (B) of 5 to 15 to 9 to 8, preferably of 5 to 8 to 8 to 12, preferably at a weight ratio of (A) to (B) of 7 to 10, in particular having a total variability of the present value of plus/minus 1, preferably of 0.5.

The monomers that are common in the field of dentistry are conceivable as further liquid monomers: Examples include radically polymerisable mono-functional monomers, such as mono(meth)acrylate, methyl-, ethyl-, butyl-, benzyl-, furfuryl- or phenyl(meth)acrylate.

Typical di-functional monomers, also referred to as crosslinker and/or multi-crosslinker, include BDMA 1,4-butandiol dimethacrylate (1,4-BDMA), bis-GMA monomer (bisphenol-A-glycidylmethacrylate) (an addition product of methacrylic acid an bisphenol-A diglycidylether), diethylene glycol dimethacrylate, bisphenol-A di(meth)acrylate, decanediol di(meth)acrylate, dodecandiol di(meth)acrylate, hexyldexandiol di(meth)acrylate, as well as butanediol di(meth)acrylate, ethylene glycol di(meth)acrylate, polyethylene glycol di(meth)acrylate, ethoxylated/propoxylated bisphenol-A-di(meth)acrylate. The following di-functional monomers may also be added as diluting agent (low viscosity acrylates, such as triethylene glycol dimethacrylate (TEGDMA) and diethylene glycol dimethacrylate (DEGMA)). Tri- and tetra-functional monomers and/or multi-crosslinker comprise trimethylolpropane tri(meth)acrylate, tris(2-hydroxyethyl)-isocyanurate triacrylate, pentaerythritol tetraacrylate. In the following, further crosslinkers are also disclosed among the polymeric particles comprising copolymers that comprise at least one (meth)acrylate monomer having two, three, four, five or six (meth)acrylate groups.

The amount of aliphatic (meth)acrylate being liquid at room temperature in the mixed, not yet polymerised prosthetic base material according to the invention, in particular comprising components (A) and (B), is, for example, 0.5% to 40% by weight, preferably 20 to 40% by weight. The aliphatic (meth)acrylate can be present either in the liquid monomer component (A) or, optionally, at least in parts in the solid component and/or powder component (B) or in both. Preferably, it is present in component (A).

Furthermore, a subject matter of the invention is a milling blank made of a prosthetic material that, preferably additionally, comprises in component (A), (B) or in (A) and (B) at least one or more substance(s) from the group consisting of fillers, pigments, stabilizers, regulators, antimicrobial additives, UV-absorbing agents, thixotroping agents, catalysts and crosslinkers. Rather small amounts of said additives—as of pigments, stabilizers and regulators—are present in the milling blank, for example, a total of 0.01 to 3.0, in particular 0.01 to 1.0% by weight, based on the total mass of the material. Suitable stabilizers include, for example, hydroquinone monomethylether or 2,6-di-tert.-butyl-4-methylphenol (BHT).

Another subject matter of the invention is a polymerisable prosthetic material for the production of the polymerised milling blank that optionally additionally has at least one initiator or at least one initiator system for autopolymerisation or hot-polymerisation, which are present in the liquid component (A), the powdered component (B) or in (A) and (B) depending on the reaction conditions and/or the polymerisation system.

The following initiators and/or initiator systems for auto- or cold-polymerisation comprise a) at least one initiator, in particular at least one peroxide and/or azo compound, in particular LPO: dilauroylperoxide, BPO: dibenzoylperoxide, t-BPEH: tert-butylper-2-ehtylhexanoate, AIBN: 2,2"-azobis-(isbutyronitrile), DTBP: di-tert-butylperoxide, and, optionally, b) at least one activator, in particular at least one aromatic amine, such as N,N-dimethyl-p-toluidine, N,N-dihydroxyethyl-p-toluidine and/or p-dimethylamino-benzoic acid diethylester, or c) at least one initiator system selected from redox systems, in particular a combination selected from dibenzoylperoxide, dilauroylperoxide, and camphorquinone with amines selected from N,N-dimethyl-p-toluidine, N,N-dihydroxyethyl-p-toluidine, and p-dimethylamino-benzoic acid diethylester, or a redox system comprising a peroxide, and a reduction agent selected from ascorbic acid, ascorbic acid derivative, barbituric acid or a barbituric acid derivative, sulfinic acid, sulfinic acid derivative, particularly preferred is a redox system comprising (i) barbituric acid or thiobarbituric acid or a barbituric acid derivative or thiobarbituric acid derivative, and (ii) at least one copper salt or one copper complex, and (iii) at least one compound having an ionic halogen atom, particularly preferred is a redox system comprising 1-benzyl-5-phenylbarbituric acid, copper acetylacetonate and benzyldibutylammoniumchloride. Particularly preferably, the polymerisation in the two-component prosthetic base material is started by a barbituric acid derivative.

Common peroxides, such as dibenzoylperoxide, dilauroylperoxide, tert-butylperoctoate or tert-butylperbenzoate are used as initiators for hot-polymerisation, but alpha, alpha ε'-azo-bis(isobutyroethylester), benzpinacol and 2,2'-dimethylbenzpinacol are also suitable.

Conceivable photoinitiators are, for example, benzoin alkylether or benzoin alkylester, benzil monoketale, acylphosphine oxide, or aliphatic and aromatic 1,2-diketo compounds, such as, for example 2,2-dialkoxyacetophenone, 9,10-phenanthrenequinone, diacetyl, furil, anisil, 4,4'-dichlorbenzil, and 4,4'-dialkoxybenzil or camphorquinone. Preferably, photoinitiators are used together with a reduction agent. Examples of reduction agents include amines, such as aliphatic or aromatic tertiary amines, for example NN-Dimethyl-p-toluidine or triethanol amine, cyanethylmethylaniline, trimethylamine, N,N-dimethylaniline, N-methyldiphenylamine, N,N-dimethyl-sym-xylidine, N,N-3,5-tetramethylaniline, and 4-dimethylamino-benzoic acid ethylester or organic phosphites. Usual photoinitiator systems include, for example, camphorquinone plus ethyl-4-

(N,N-dimethylamino)benzoate, 2-(ethylhexyl)-4-(N,N-dimethylamino)benzoate, or N,N-dimethylaminoethylmethacrylate.

For polymerisation initiated by UV-light, 2,4,6-trimethylbenzoyldiphenylphosphine oxide is particularly well-suited as initiator. UV-photoinitiators can be used alone, in combination with an initiator for visible light, an initiator for cold-curing, and/or an initiator for hot-polymerisation.

Dual-curing systems can also be used, for example, photo initiators with amines and peroxides. The initiators are preferably used in amounts of 0.01 to 1% by weight, based on the total composition.

The invention also relates to a method for the production of a milling blank comprising polymerised prosthetic material, as well as a milling blank or three-dimensional moulded body obtainable by the method, in which the components A) at least one liquid monomer component, and B) at least one powdered component are being mixed and subsequently polymerised and/or cured.

Particularly preferably, A) the liquid monomer component comprises methylmethacrylate, butanediol methacrylate and, optionally, at least one methacrylate-based di-, tri- and/or tetra-functional monomer as multi-crosslinker, such as, for example, tris(2-hydroxyethyl)-isocyanurate triacrylate and/or pentaerythritol tetraacrylate, as well as one urethane diacrylate, at least a part of an initiator system, and B) comprises PMMA beads, barbituric acid or a barbituric acid derivative, as well as, optionally, pigments. To produce the prosthetic base material, components A) and B) are mixed.

According to a preferred variant of the method the A) monomer component and the B) powdered component are being mixed at a weight ratio of 1:50 to 50:1, in particular at a weight ratio of 7:10 (150 g powder to 105 ml liquid, or 10 g powder, 7 ml liquid, having similar density), in particular with a total variability of the present value of plus/minus 1, preferably plus/minus 0.5. The ratio powder to liquid is about 1.35 to 1.5 to 1, preferably, the weight ratio is about 1.4-1.5 to 1 of powder to liquid.

The mixing of components A) and B) can be carried out according to the invention by means of simple measures known to the dental technician, such as by means of spatula.

Another subject matter of the invention is a pigmented milling blank made of polymerised prosthetic base material. Furthermore, a subject matter of the invention is a milling blank made of unpigmented, polymerised prosthetic base material having a transparency of greater than or equal to 85%, in particular greater than 90% (measured against 3 mm plates having a height of 3 mm).

According to a further embodiment, a subject matter of the invention is the use of core-shell particles modified by at least one elastic phase and at least one urethane di(meth)acrylate or one derivative of an urethane di(meth)acrylate in auto- or cold-polymerisable prosthetic materials for the production of milling blanks.

The invention also relates to the use of core-shell particles, modified by at least one elastic phase, in prosthetic materials and, optionally, in prosthetic materials comprising at least one urethane dimethacrylate, for the production of milling blanks or half-finished products, or half-finished product moulds of milling blanks, in particular for the production of dental milling blanks or orthopedic milling blanks, In this context, the production of CNC- and/or CAD/CAM milling blanks ist particularly preferred.

Furthermore, a subject matter of the invention is the use of a milling blank, in particular having core-shell particles modified by at least one elastic phase and, optionally, comprising an urethane methacrylate, for the production of components, in particular of dental or orthopedic components, comprising prosthesis base plates, occlusal splints, crowns, bridges, artificial teeth, veneers, inlays, onlays, orthodontic appliances, active or passive orthodontic appliances, Crozat-appliances, modified activators, implants, superstructures, dental bars, abutments, dental fastening means, dental screws, surgical guides for implantology, telescopic prostheses and telescopic crowns, mouthguards, artificial articular protheses, braces, double bite jumping plates, implant parts, invisible braces, brackets, multibracket appliances, orthodontic instruments, and/or multiband appliances, or of at least parts of the afore-mentioned components, or in the veterinary field, in particular for hoof repair components.

According to a further alternative, a subject matter of the invention is a Kit comprising an autopolymerisable prosthetic material, whereby the Kit comprises separated components (A) and (B), for the production of milling blanks.

Auto- or cold-polymerisable according to the invention shall be understood to mean a prosthetic material meeting the criteria according to ISO 20795-1 (Pt. 3.1). Cold-polymerising plastic materials shall be understood to mean compositions, which polymerise below 65° C. Preferably, cold-polymerising prosthetic materials according to the invention can independently cure and/or polymerise in a temperature range from 50° C. to 65° C., preferably from 50° C. to 60° C., more preferably from 50° C. to 55° C., after mixing components (A) and (B). According to the afore-mentioned norm, polymerisable compositions, which independently cure and/or polymerise above 65° C., are referred to as heat-curing compositions.

The powder component of two-component prosthetic base material usually comprises a polymer powder, in particular based on methacrylate, and/or a bead polymer based on methacrylate. In this field, beat polymers are often referred to as powder.

Bead polymers, in particular those made of (meth)acrylates, are known to the person skilled in the art. Bead polymers basing on polyalkyl(meth)acrylates are obtained in known manner through precipitation polymerisation or suspension polymerisation. In this context, suspension polymerisation usually yields larger particles. The average particle sizes vary over a wide range and can be, for example, from 0.1 µm to 250 µm. Cross-linking bead polymers are conceivable as well. Suitable multi-functional crosslinker molecules are evident from the listing of common monomers that are common in dentistry provided above. Further comonomers can also be polymerised into the bead polymers, as explained above.

In a preferred embodiment, crosslinkers have been polymerised, at least in part, into the beads of the first (co)polymer and/or into the beads of the second (co)polymer. Accordingly, the first and second bead polymers also comprise cross-linked and partly cross-linked bead polymers.

For cross-linking, it is common to resort to multi-functional comonomers or multi-functional oligomers. Aside from di-, tri- and poly-functional (meth)acrylates, graft crosslinkers having at least two different reactive C—C double bonds, for example, alkylmethacrylates and alkylacrylates, as well as aromatic crosslinkers, such as 1,2-divinylbenzene, 1,3-divinylbenzene, and 1,4-divinylbenzene, are suitable for this purpose. Amongst the difunctional (meth)acrylates, in particular, the (meth)acrylates of propandiol, butanediol, hexandiol, octandiol, nonandiol, decandiol, and eicosandiol, as well as the di(meth)acrylates of ethylene glycol, triethylene glycol, tetraethylene glycol, dodecaethylene glycol, tetradecanethylene glycol, propylene glycol, dipropylene glycol, and tetradecanpropylene glycol, moreover glycerol di(meth)acrylate, 2,2-bis[(gamma-methacryloxy-beta-oxypropoxy)-phenylpropane], bis-GMA, bisphenol-A dimethacrylate, neopentylglycol di(meth)acrylate, 2,2-(di-methacryloxypolyethoxy-phenyl) propane with 2 to 10 ethoxy groups per molecule, as well as 1,2-bis(3-methacryloxy-2-hydroxypropoxy)butane, shall be mentioned. Exemplary, multi-functional (meth)acrylates include, for example, di-, tri- and/or tetra(meth)acrylates, such as 1,4-butandiol dimethacrylate, ethylene glycol dimethacrylate, as well as di- or trivinylic compounds, such as divinylbenzene.

The content of said crosslinker molecules in the starting mixture of the bead polymer is in the range from 0.1% by weight to 10% by weight, in particular in the range from 0.5% by weight to 5% by weight.

In an expedient embodiment, at least one crosslinker is present in liquid component (A) aside from at least one of the afore-mentioned mono-functional alkylmethacrylate monomers. This can be, for example, multi-functional monomers, comonomers or multi-functional oligomers. Aside from di-, tri- and poly-functional (meth)acrylates, graft crosslinkers having at least two different reactive C—C double bonds, for example, alkylmethacrylates and alkylacrylates, as well as aromatic crosslinkers, such as 1,2-divinylbenzene, 1,3-divinylbenzene and 1,4-divinylbenzene, are suitable for this purpose. Amongst the difunctional (meth)acrylates, in particular, the (meth)acrylates of propandiol, butanediol, hexandiol, octandiol, nonandiol, decanediol, and eicosandiol, as well as the di(meth)acrylates of ethylene glycol, triethylene glycol, tetraethylene glycol, dodecaethylene glycol, tetradecanethylene glycol, propylene glycol, dipropylene glycol, and tetradecanpropylene glycol, moreover glycerol di(meth)acrylate, 2,2-bis[(gamma-methacryloxy-beta-oxypropoxy)-phenylpropane], bis-GMA, bisphenol-A dimethacrylate, neopentylglycol di(meth)acrylate, 2,2-(di-methacryloxypolyethoxy-phenyl) propane with 2 to 10 ethoxy groups per molecule, as well as 1,2-bis(3-methacryloxy-2-hydroxypropoxy)butane, shall be mentioned. Exemplary, multi-functional (meth)acrylates include, for example, di-, tri- and/or tetra(meth)acrylates, such as 1,4-butandiol dimethacrylate, ethylene glycol dimethacrylate, as well as di- or trivinylic compounds, such as divinylbenzene. It is self-evident that mixtures of said crosslinker molecules can be used as well. Such multi-functional compounds, in particular di- and/or tri-functional compounds, that possess elastic elements and are therefore suitable for imparting flexible properties on prosthetic materials that are obtained from prosthetic starting materials, are particularly suitable as well.

Exemplary, Dimethacrylates, such as 1,4-butanediol dimethacrylate, are to be mentioned. Said crosslinker molecules can be present in liquid component (A) in amounts in the range from 0.1 to 20% by weight, preferably in the range from 1 to 10% by weight, for example, 5% by weight.

In another embodiment, liquid component (A) may contain further comonomers aside from, for example, methylmethacrylate as the preferred main monomer (>50% by weight).

The radical initiator system required for polymerisation is contained in liquid component (A) and/or powdered component (B) depending on reaction conditions and/or polymerisation system. Pertinent details are known to the person skilled in the art. For example, in base mixtures for cold-cure polymers, the initiator system is most often present in both components, the liquid component and the powdered component, and is thus combined when mixing said components. Accordingly, one initiator component (c) is usually present in powdered component (B), in particular in the form of peroxides, perketals, peresters and/or azo compounds. Another part of the initiator system (c), usually a co-initiator, can be present in liquid component (A). It is also feasible to use as initiators residual contents of initiator components that did not react during production of the powdered components, for example, peroxides, such as dibenzoylperoxide.

Conceivable initiators for the polymerisation reaction of cold and/or auto-polymerising starting mixtures are basically those that can be used to initiate radical polymerisation reactions. Preferred initiators are peroxides, as well as azo compounds, such as, for example, the following: LPO: dilauroylperoxide, BPO: dibenzoylperoxide, t-BPEH: tert-butylper-2-ethylhexanoat, AIBN: 2,2'-azobis-(isobutylnitrile), DTBP: di-tert-butylperoxide.

Suitable activators, for example, aromatic amines, can be added to accelerate the radical polymerisation through peroxides. Exemplary, N,N-dimethyl-p-toluidine, N, N-dihydroxyethyl-p-toluidine, and p-dibenzylamino-benzoic acid diethylester are to be mentioned as suitable amines. In this context, the amines usually function as co-initiators and are usually present in an amount of up to 0.5% by weight.

The afore-mentioned redox systems are suitable as radical initiator systems. In an expedient embodiment, a redox system of this type comprises barbituric acid or thiobarbituric acid, or a barbituric acid or thiobarbituric acid derivative (for example 25 to 80% by weight), at least one copper salt or copper complex (for example 0.1 to 8% by weight), and at least one compound having an ionogenic halogen atom (for example 0.05 to 7% by weight). Exemplary, suitable ingredients of the afore-mentioned redox system are 1-benzyl-5-phenylbarbituric acid, copper acetylacetonate, and benzyl dibutylammoniumchloride.

Curing of the polymerisable prosthetic materials preferably proceeds through redox-induced radical polymerisation at room temperature and/or at slightly elevated temperature and under a slight pressure in order to avoid the formation of bubbles. Examples of suitable initiators for polymerisation performed at room temperature include redox initiator combinations, such as, for example combinations of benzoyl- or laurylperoxide with N,N-dimethyl-sym-xylidine or N,N-dimethyl-p-toluidine. A particularly preferred initiator system consists of a combination of barbituric acid in conjunction with copper and chloride ions, as well as above-mentioned peroxides. Said system is characterised by its high level of colour-stability.

Furthermore, the powdered component (B) and/or the liquid component (A) can be provided in known manner with further additives from the group of stabilizers, UV-absorbing agents, thixotroping agents and fillers.

The subject matter of the invention is illustrated in more detail by FIGS. 1a to d, without meaning to thus limit the invention to these embodiments.

As depicted above, the milling blank according to the invention can preferably be tooth-coloured, colour-adjusted to the gingiva, or be designed multi-coloured in certain areas. For setting the tooth colour, and/or the colour and/or colour gradients of the gingiva, colour pigments can be added to the polymerisable prosthetic material, or be contained in the prosthetic material of the milling blank:

FIG. 1a and FIG. 1b: SEM—images of the core-shell particles (left: 100×, right: 10,000×); FIGS. 1c and d: SEM-image of the additive being suspended in MMA and dried prior to the image (left: 500×, right: 10,000×); FIGS. 2a and 2b—examples for milling blanks (0)

EXEMPLARY EMBODIMENT

Producing the Powder Mixture (B) According to the Invention:

A mixture is produced from PMMA beads of different grain sizes (bead 1 homopolymer ($d_{50}$~40-50 μm) 60-70%, bead 2 ($d_{50}$~55-70 μm) 15%, bead 3 copolymer (d50~40-50 μm) 15%) with the addition of barbituric acid and colour pigments.

Producing the Liquid/Monomer Mixture (A) According to the Invention:

A mixture is produced from methylmethacrylate, and another methacrylate-based multi-crosslinker with the addition of stabilizers and initiators (barbituric acid/copper-system). In addition, the urethane dimethacrylate according to the invention, as well as the core-shell particles according to the invention are being added.

Example according to the invention powder mixture and liquid mixture:

| Liquid | Example 1 |
|---|---|
| methylmethacrylate | 93.3 |
| 2-(4,6-diphenyl-1,3,5-triazine-2-yl)-5-((hexyl)oxy)-phenol | 0.3 |
| N-methyl-N,N-dioctyloctane-1-ammoniumchloride | 0.2 |
| solution of copper(II) chloride | 0.1 |
| N,N-Bis(2-hydroxyethyl)-p-toluidine | 0.1 |
| total | 94.00 |
| di-functional aliphatic urethane acrylate oligomer | 3.00 |
| tris(2-hydroxyethyl)-isocyanurate triacrylate | 1.00 |
| core-shell particles | 2.00 |
| total | 100.00 |

| Powder | |
|---|---|
| PMMA/PMA $d_{50}$~40-45 μm | 67.5 |
| PMMA $d_{50}$~40-55 μm | 15.000 |
| cross-linked PMMA $d_{50}$~55-70 μm | 15.000 |
| phenylbenzylbarbituric acid | 2.5 |
| total | 100.000 |

TABLE 1

Comparison of the example according to the invention and the comparative examples
Physical properties (Norm ISO 20795-1)

| | Example 1 | | PMMA |
|---|---|---|---|
| flexural strength [MPa] | >60 | 71.1 | 85.9 |
| E-modulus [MPa] | >1500 | 2389 | 2518 |
| fracture toughness [MPa m1/2] | >1.9 | 2.36 | 1.42 |
| total fracture work [J/m²] | >900 | 1030.85 | 197.64 |
| transparency [delta %] (after 6 d/37° C. of storage in Ringer's solution) | | | −3.16 |

Production of Test Bodies, Determination of Colour Values, Determination of Mechanical Properties:

Colour Test Bodies:

The following powder mixtures and monomer mixtures at a ratio of 10 g powder to:7 ml liquid are being vigorously mixed and test bodies with dimensions of 30×30×3 mm are being poured after the swelling phase (approximately 5 min at 23° C.) and being polymerised in Palamat elite for 30 min at 55° C. and 2 bar pressure.

Test Bodies for Mechanical Strength:

The following powder mixtures and monomer mixtures at a ratio of 150 g powder:105 ml liquid are being vigorously mixed for about 30 seconds and test bodies are being poured into a metal mould after the swelling phase (approximately 3 min at 23° C.). The metal mould brass tube closed at one side having an inner diameter of 102 mm and a height of 50 mm. The polymerisation proceeds in a pressure pot Palamat elite for 30 min at 55° C. and 3.8 bar pressure.

The test bodies are being milled out of the received milling blank by means of CAD/CAM according to the requirements of ISO 20795-1 and tested.

Test bodies for colorimetric tests are produced in duplicating gels.

To determine the transparency, the test bodies are stored for 5 days in Ringer's solution at 37° C., and the colour values and transparency are determined both before and after storage using 3 mm-plates. The measurements of table 1 are made according to DIN EN ISO 20795-1.

The monomer mixture according to the invention shows significantly improved fracture toughness over all comparative examples, increased transparency, as well as the least loss of transparency after storage in Ringer's solution (reduced tendency to whitening).

The invention claimed is:

1. Milling blank made of polymeric prosthetic material, wherein the prosthetic material is present in the form of a three-dimensional moulded body, optionally being suitable for ablative machining, suitable as a CAD/CAM (computer-aided design/computer-aided manufacturing) milling blank, wherein the moulded body comprises (A) at least one polymer comprising 0.001 to 10% by weight of the moulded body of at least one urethane acrylate or urethane methacrylate polymerized into the polymer and (B) 0.001 to 10% by weight of the moulded body of core-shell particles modified by at least one elastic phase, whereby the moulded body has a fracture toughness of ≥1.9 Mpa m$^{1/2}$ and a total fracture work of ≥900 J/m².

2. Milling blank according to claim 1, wherein the core-shell particles comprise primary particles, whereby the primary particle size has an average particle size of less than or equal to $d_{50}$≤500 nm to 10 nm.

3. Milling blank according to claim 1, wherein the core-shell particles comprise aggregates of primary particles, whereby the aggregates have an average particle size of less than or equal to ($d_{50}$) 400 μm (micrometers).

4. Milling blank according to claim 1, wherein the distribution of the elastic phase in the modified core-shell particles is selected from possibilities a to d:
a) elastic phase as core in solid outer shell (core-shell-particles);
b) multiple elastic phases as cores in a solid matrix;
c) core-shell particles from a) distributed in solid matrix, and
d) solid core with elastic phase as outer shell.

5. Milling blank according to claim 1, wherein the unpigmented prosthetic material has a transparency of greater than or equal to 90% (measured against plates having a height of 3 mm).

6. Milling blank according to claim 1, which additionally comprises one or more substance(s) from the group consisting of fillers, pigments, stabilizers, regulators, antimicrobial additives, UV-absorbing agents, thixotroping agents, catalysts and crosslinkers.

7. Milling blank according to claim 1, which is single-coloured in tooth colours or is colour-adjusted to the gingiva, or the milling blank is designed multi-coloured, wherein defined areas are designed tooth-coloured and/or defined areas are designed colour-adjusted to the gingiva.

8. Milling blank according to claim 1, which comprises greater than or equal to 55% by weight PMMA (polymethylmethacrylate), based on the total composition.

* * * * *